(12) United States Patent
Nelson et al.

(10) Patent No.: US 11,832,835 B1
(45) Date of Patent: Dec. 5, 2023

(54) FECAL IMPACT REMOVER TOOL AND METHOD OF USING THEREOF

(71) Applicants: Lerrlyn Nelson, Detroit, MI (US); Patrick Munson, Bitley, MI (US)

(72) Inventors: Lerrlyn Nelson, Detroit, MI (US); Patrick Munson, Bitley, MI (US)

( * ) Notice: Subject to any disclaimer, the term of this patent is extended or adjusted under 35 U.S.C. 154(b) by 0 days.

(21) Appl. No.: 18/457,300

(22) Filed: Aug. 28, 2023

Related U.S. Application Data (63) Continuation-in-part of application No. 17/457,656, filed on Dec. 4, 2021.

(51) Int. Cl.
*A61B 17/22* (2006.01)
*A61K 9/02* (2006.01)

(52) U.S. Cl.
CPC ............... *A61B 17/22* (2013.01); *A61K 9/02* (2013.01); *A61B 2017/22037* (2013.01); *A61B 2017/22079* (2013.01); *A61B 2017/22084* (2013.01); *A61B 2217/007* (2013.01)

(58) Field of Classification Search
CPC ............... A61M 3/02; A61B 10/0038; A61B 17/22012; A61B 17/22; A61B 2217/007; A61B 2017/22084; A61B 2017/22079; A61B 2017/22037; A61F 5/442; A61K 9/02
See application file for complete search history.

(56) References Cited

U.S. PATENT DOCUMENTS

| | | | |
|---|---|---|---|
| 4,143,130 A | 3/1979 | Imondi | |
| 5,000,750 A * | 3/1991 | LeVeen | A61B 90/00 606/1 |
| 10,857,326 B2 | 12/2020 | Kelly | |
| 11,185,625 B2 | 11/2021 | Hassidov | |
| 2004/0019295 A1* | 1/2004 | Zhou | A61B 10/0096 600/562 |
| 2019/0240060 A1 | 8/2019 | He | |
| 2020/0178988 A1 | 6/2020 | Henry et al. | |

* cited by examiner

*Primary Examiner* — Jocelin C Tanner
(74) *Attorney, Agent, or Firm* — Nexus Law PLLC (57) ABSTRACT

A tool for removing fecal impaction in a patient includes a housing having a front portion, a main body, and a rear portion. The front portion is configured for at least a partial insertion into the patient. The housing includes an internal repository and an inner duct extending from the rear portion to the front portion. The tool further includes a screw trocar having a front end and a rear end, the screw trocar can be rotatably and removably inserted into the housing to extend along the inner duct of the housing, and a suppository trocar having a front end and a rear end, the suppository trocar can be removably inserted into the housing to extend along the inner duct of the housing. The housing is configured to receive one of the screw or suppository trocars at a time to effectuate removal of fecal impaction in the patient.

20 Claims, 5 Drawing Sheets

FECAL IMPACT REMOVER TOOL AND METHOD OF USING THEREOF

CROSS REFERENCE TO RELATED APPLICATION

The present application is a continuation-in-part of application Ser. No. 17/457,656, filed Dec. 4, 2021, which is hereby incorporated herein by reference in its entirety.

FIELD OF THE INVENTION

The present invention relates in general to a medical appliance, and more particularly to a tool and a method of using thereof for removing fecal impact in a patient.

BACKGROUND OF THE INVENTION

Fecal impaction is a medical condition in which a large mass of hardened stool becomes stuck in the rectum and colon, making it difficult or impossible to pass. This condition typically occurs when constipation becomes severe and the stool becomes extremely hard and dry. Fecal impaction can cause a range of symptoms and complications, including abdominal discomfort, difficulty passing stool, rectal bleeding, overflow incontinence, pelvic pain, urinary issues, etc.

Fecal impaction is more common in older adults, people with certain medical conditions (such as neurological disorders), and individuals who are bedridden or have limited mobility. It's important to seek medical attention whenever one is suspected to have fecal impaction, as it can lead to serious complications like bowel perforation or infection.

Treatment for fecal impaction generally involves medical intervention to soften the stool and facilitate its passage. The most common methods known today to treat fecal impaction include laxatives, enemas, manual removal of the impacted stool by a medical professional, and dietary changes to prevent recurrence. None of the above-mentioned methods, however, provide for quick and effective relief for the patient and ease and convenience of providing such treatment to the patient for a medical professional.

SUMMARY OF THE INVENTION

The following presents a simplified summary in order to provide a basic understanding of some aspects of the invention. The summary is not an extensive overview of the invention. It is neither intended to identify key or critical elements of the invention nor to delineate the scope of the invention. The following summary merely presents some concepts of the invention in a simplified form as a prelude to the description below.

The present invention provides for a tool that is easy and convenient to use by a medical professional or a caregiver and effective in providing a quick relief for the patient suffering from fecal impaction. Further, the present invention provides for a method that is safe and practical for physical removal of fecal impaction by a clinician or a caregiver of any level to provide relief to the patient suffering from or having discomfort associated with fecal impaction.

The tool for removing fecal impaction in a patient provided by the present invention includes a housing and insertion, screw, and suppository trocars, which when used with the housing sequentially can effectively remove fecal impaction in the body of a patient.

In one form of the present invention, the tool for removing fecal impaction in a patient includes a housing having a front portion, a main body, and a rear portion, where the front portion is configured for at least a partial insertion into the patient. The front portion includes a front opening and the rear portion includes a rear opening. The housing includes an internal repository and an inner duct extending from the rear opening to the front opening. The tool further includes an insertion trocar having a front end and a rear end. The insertion trocar can be removably inserted into the housing to extend along the inner duct of the housing. The tool also includes a screw trocar having a front end and a rear end, the screw trocar can be rotatably and removably inserted into the housing to extend along the inner duct of the housing, and a suppository trocar having a front end and a rear end, the suppository trocar can be removably inserted into the housing to extend along the inner duct of the housing. The housing is configured to receive one of the insertion, screw or suppository trocars at a time to effectuate removal of fecal impaction in the patient.

According to one aspect, the tool further includes a lid that is configured to securely cover the rear opening of the housing, the lid including a central opening and a port. The port is configured to be connected to a medical suction device.

According to another aspect, the rear end of the insertion trocar includes a handle and the front end of the insertion trocar includes a rounded tip configured to extend a distance past the front portion of the housing when the insertion trocar is fully inserted into the housing.

According to a further aspect, the front end of the screw trocar includes one or more spiral or helical blades and one or more irrigation openings. The rear end of the screw trocar includes a handle.

According to yet a further aspect, the screw trocar includes an internal canal that extends along a length of the screw trocar and is in fluid communication with the one or more irrigation openings. The internal canal extends through the handle of the screw trocar to form a central opening in the handle.

According to yet another aspect, the internal repository is disposed within the main body of the housing. The inner duct extends through the internal repository of the housing, and the internal repository receives fecal matter of the patient when the screw trocar is fully inserted and rotated in the inner duct of the housing.

According to still a further aspect, the suppository trocar includes a sheath and a plunger, the sheath having a tubular passage therethrough and the plunger having a shaft that can be removably inserted into the tubular passage of the sheath to extend along a length of the sheath. The sheath includes a front end and a rear end, the front end having a front opening of a first diameter and the rear end having a rear opening of a second diameter. The rear opening of the sheath is configured to removably receive the shaft of the plunger and the front opening of the sheath is configured to removably receive a suppository. The shaft of the plunger includes a front end and a rear end. The rear end of the shaft includes a handle and one or more tabs each outwardly extending from the handle and along the shaft.

Aspects of the present specification disclose a multi-component tool for physically removing fecal impaction in the body of a patient in a safe, painless, convenient and practical manner, which also eliminates unpleasant and inconvenient manual removal procedures for the medical staff. These and other objects, advantages, purposes and features of the present invention will become apparent upon review of the following specification in conjunction with the drawings.

BRIEF DESCRIPTION OF THE DRAWINGS

The drawings are not necessarily to scale and, in some instances, proportions have been exaggerated in order to more clearly depict certain features of the invention.

DETAILED DESCRIPTION OF PREFERRED EMBODIMENTS

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout. Throughout this disclosure, unless the context dictates otherwise, the word "comprise" or variations such as "comprises" or "comprising," is understood to mean "includes, but is not limited to" such that other elements that are not explicitly mentioned may also be included. Further, any terms expressed in the singular form herein are meant to also include the plural form and vice versa, unless explicitly stated otherwise. Also, as used herein, the term "a" and/or "an" shall mean "one or more," even though the phrase "one or more" is also used herein.

Figure 11A:
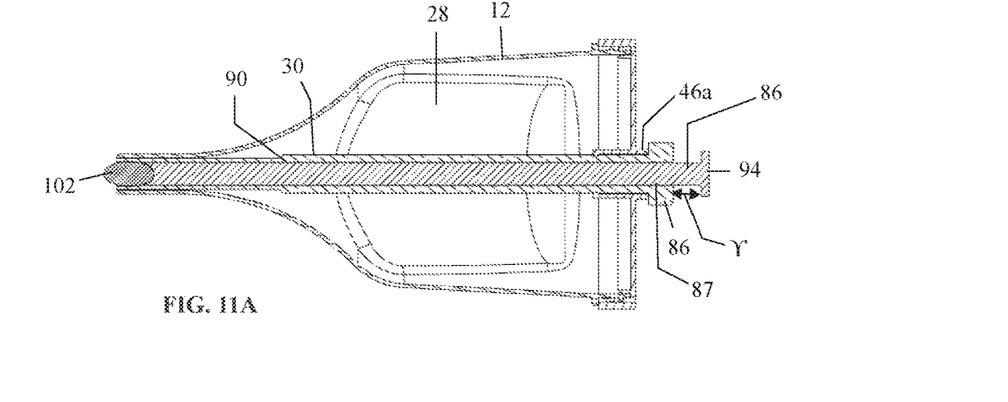
FIG. 11A is a cross-sectional side elevation view of the tool illustrated in FIG. 10, taken along line XI-XI, and shown with the suppository trocar holding a suppository and not being fully inserted into the tool.
Figure 11B:
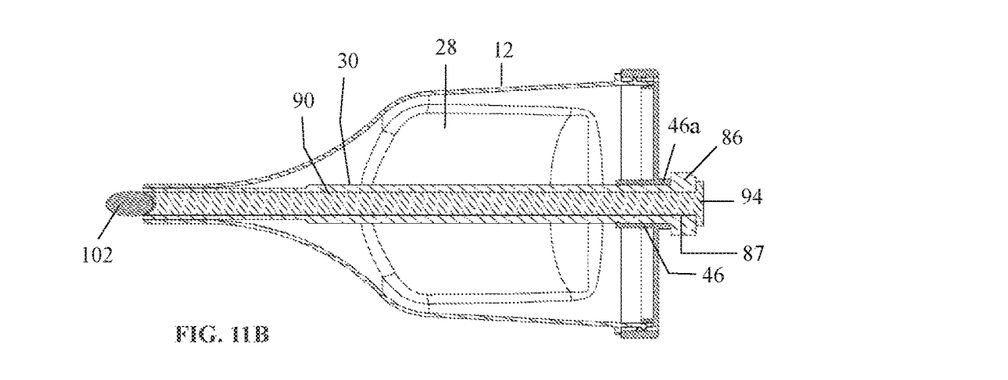
FIG. 11B is a cross-sectional side elevation view of the tool illustrated in FIG. 10, taken along line XI-XI, and shown with the suppository trocar releasing the suppository when being fully inserted into the tool.
Figure 12:
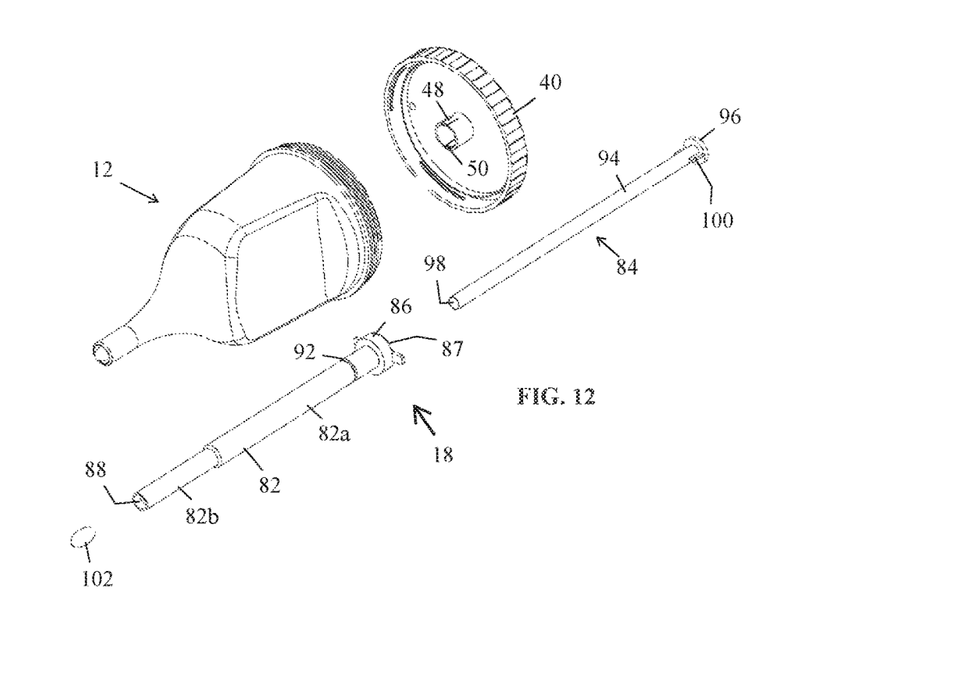
FIG. 12 is an exploded perspective view of the tool illustrated in FIG. 9.

Referring now to the drawings and the illustrative embodiments depicted therein, a tool 10 of the present invention for removing fecal impaction in a patient (not shown) is illustrated in FIGS. 1-12. The tool 10, which is preferably made from a medical grade plastic, includes a collection bulb or housing 12, an insertion trocar 14 (FIG. 4), a screw trocar 16 (FIG. 8) and a suppository trocar 18 (FIG. 12).

Figure 1:
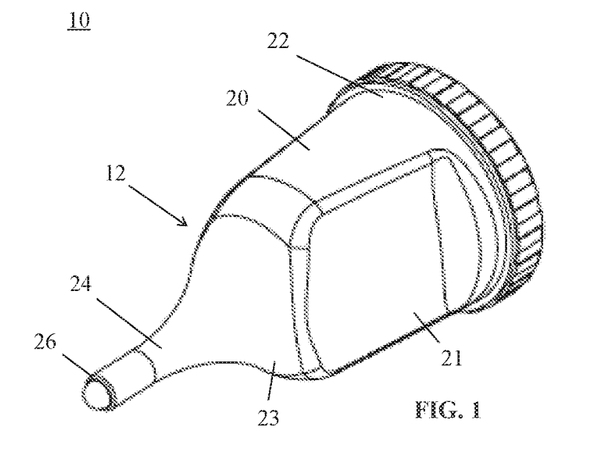
FIG. 1 is a perspective view of a tool for removing fecal impaction in a patient with an insertion trocar being inserted into the tool, in accordance with an embodiment of the present invention.
Figure 2:
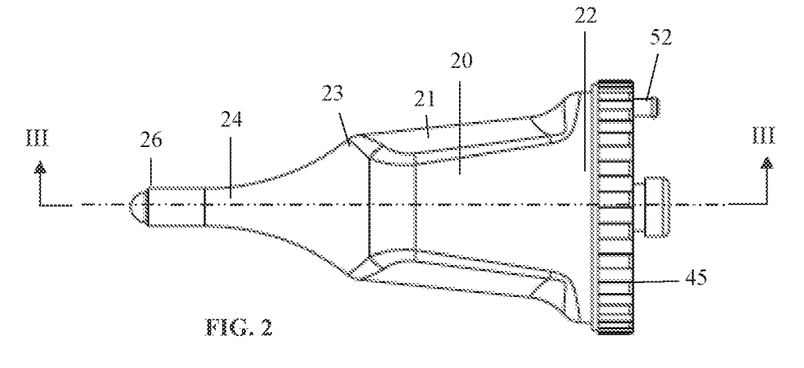
FIG. 2 is a top plan view of the tool illustrated in FIG. 1.

Although it is contemplated that the housing 12 can be formed in a variety of shapes, such as for example a conical shape, the housing 12 of the illustrated embodiment has a bulb-like or bell-like shape and comprises a main body 20, a rear portion 22 and a front portion 24. As can be seen in FIG. 2, the main body 20 has indented regions 21 on opposite sides of the main body 20 for more convenient gripping, holding or manipulation of the tool 10. However, other forms, designs and shapes of the main body 20 are also possible. Preferably, the housing 12 is formed of a clear or transparent plastic material to enable a user to view inside the housing. The front portion 24 of the housing 12 has a tubular, elongated and pointed shape that is formed with a wider diameter in a region 23 near the main body 20 and narrowing down towards a tip 26. It should be appreciated that as the diameter of the front portion 24 narrows from the region 23 towards the tip 26, a smooth inwardly curvature is formed to facilitate relatively smooth penetration of the tool 10 into the body of a patient. Further, the housing 12 or the front portion 24 can come in different sizes to accommodate kids or adults.

Figure 3:
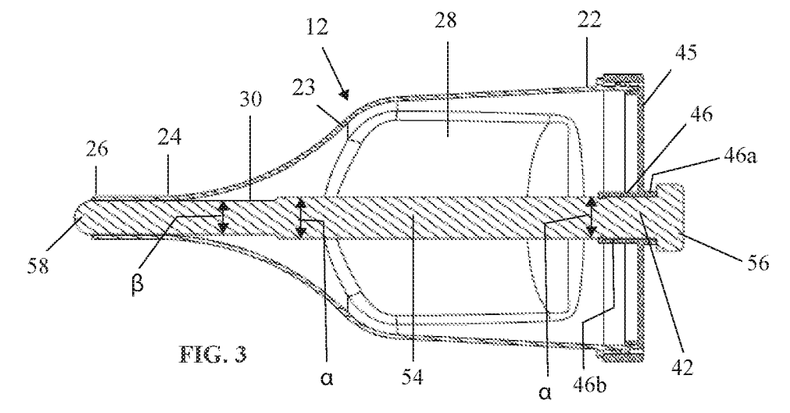
FIG. 3 is a cross-sectional side elevation view of the tool illustrated in FIG. 2, taken along line III-III.
Figure 4:
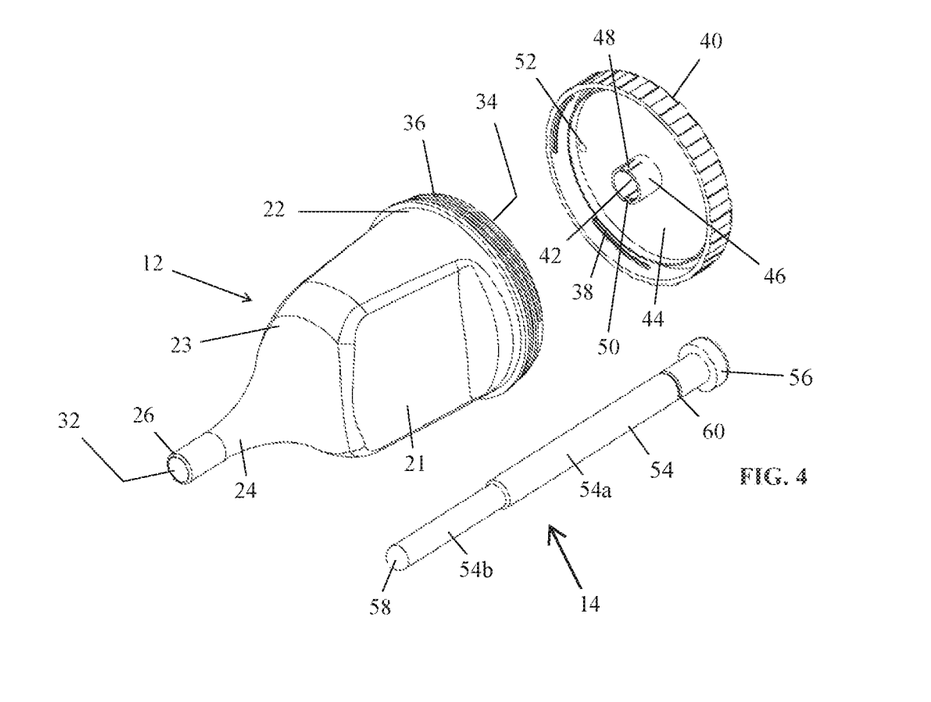
FIG. 4 is an exploded perspective view of the tool illustrated in FIG. 1.
Figure 5:
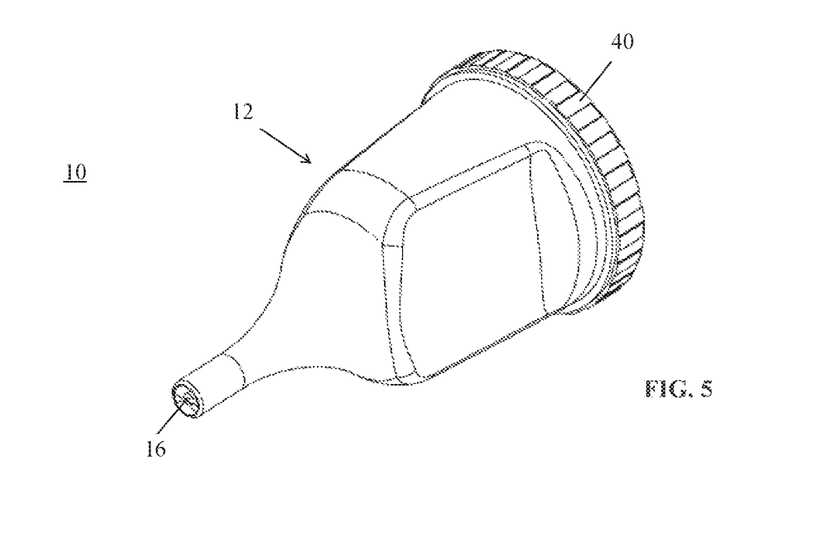
FIG. 5 is a perspective view of the tool of FIG. 1 with the insertion trocar being taken out and a screw trocar being inserted into the tool, in accordance with the present invention.
Figure 6:
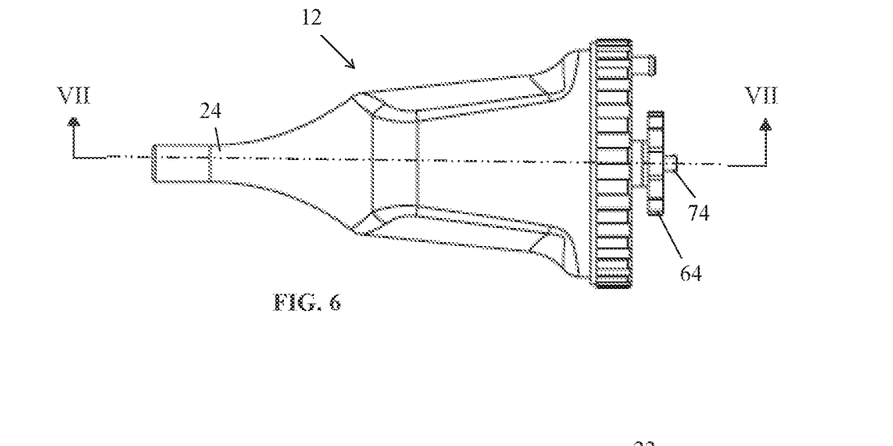
FIG. 6 is a top plan view of the tool illustrated in FIG. 5.

The housing 12 includes a hollow internal repository 28 and an inner duct 30 that extends from the rear portion 22, through the internal repository 28, and to the tip 26 of the front portion 24, as shown for example in FIG. 3. As the duct 30 extends through the housing 12, it has varying diameters. As best shown in FIG. 3, the duct 30 has diameter a in the rear portion 22 and the region 23 of the housing 12 and diameter β in the front portion 24. The diameter of the duct 30 extending within the internal repository 28 is defined by a diameter of the internal repository 28. The tip 26 includes an aperture 32, as shown in FIG. 4, that is in fluid communication with the inner duct 30 and has an internal diameter that is similar to diameter β of the inner duct 30. The rear portion 22 of the housing 12 includes a rear opening 34 that provides access to the internal repository 32 and is in fluid communication with the inner duct 30 and internal repository 32. As shown in FIG. 4, the rear portion 22 further includes a region having external threads 36 that are configured to engage internal threads 38 of a lid 40, which is configured to securely cover the rear opening 34.

In the illustrated embodiment of FIGS. 1-12, the lid 40 has a generally circular shape, however, other shapes are possible to accommodate other possible shapes of the rear portion 22 of the housing 12. The lid 40 includes a central opening 42, as shown in FIGS. 3 and 4. The central opening 42 includes a hollow tubular sleeve 46 extending therethrough. The sleeve 46 has a shorter upper portion 46a outwardly extending from a top surface 45 of the lid 40 and a longer bottom portion 46b extending from a bottom surface 44 of the lid 40. It is noted that the bottom surface 44 faces the internal repository 28 when the lid 40 covers the rear opening 34 of the housing 12. The bottom portion 46b of the sleeve 46 is formed to include a pair of opposing tabs 48 disposed within the circumference of the bottom portion 46b of the sleeve 46. Each of the pair of tabs 48 has a free distal end that includes a detent 50 extending some distance into the hollow area of the sleeve 46 and towards one another. It should be noted that an internal diameter of the sleeve 46 is envisioned to be similar to diameter α of the inner duct 30.

As can be seen in FIGS. 2 and 4, the lid 40 is further envisioned to include a port 52 that extends outwardly from a top surface 45 (FIG. 2) of the lid 40 and is in fluid communication with the internal repository 28. The port 52 is configured for connection to, for example, a medical suction device (not shown) to extract or evacuate fecal matter and/or irrigation fluid or liquid, which will be described in more detail below, from the internal repository 28.

With reference to FIGS. 1-4, the insertion trocar 14, as best shown in FIG. 4, comprises a generally circular shaft 54, one end of which including a ring or handle 56 and an opposing end including a rounded tip 58. A substantially longer portion 54a of the shaft 54 has a diameter that is larger than a diameter of the shorter portion 54b of the shaft 54. It should be apparent that the diameter of the longer portion 54a corresponds to diameter α in the rear portion 22 and the region 23 of the housing 12, and the diameter of the shorter portion 54b corresponds to diameter β in the front portion 24. As such, the longer and shorter portions 54a, 54b of the shaft 54 are configured to fit inside the duct 30 with minimal or no friction, though some interference fit is possible.

When the insertion trocar 14 is fully inserted into the housing 12, as shown in FIG. 3, the tip 58 is configured to extend through and some distance past the aperture 32 of the tip 26. The longer portion 54a of the shaft 54 further includes a notch 60 disposed some distance away and being proximal to the handle 56 of the insertion trocar 14. As can be best seen in FIG. 4, the notch 60 extends around the circumference of the longer portion 54a of the shaft 54.

As shown in FIG. 3, when the insertion trocar 14 is fully inserted into the housing 12, i.e., through the central opening 42 in the lid 40 and all the way along the duct 30 of the housing 12, the notch 60 aligns with and is configured to engage the detents 50 of the pair of tabs 48. As such, the detents 50 engaged with the notch 60 prevent or limit the insertion trocar 14 from having a free or unobstructed linear movement along the duct 30, meanwhile allowing the insertion trocar to rotate within the duct 30 of the housing 12. It should also be noted that the insertion trocar 14 is fully inserted when the handle 56 abuts the upper portion 46a of the sleeve 46. Thus, the handle 56 also serves as a stopper that limits a further linear movement of the insertion trocar 14 through the aperture 32.

Figure 7:
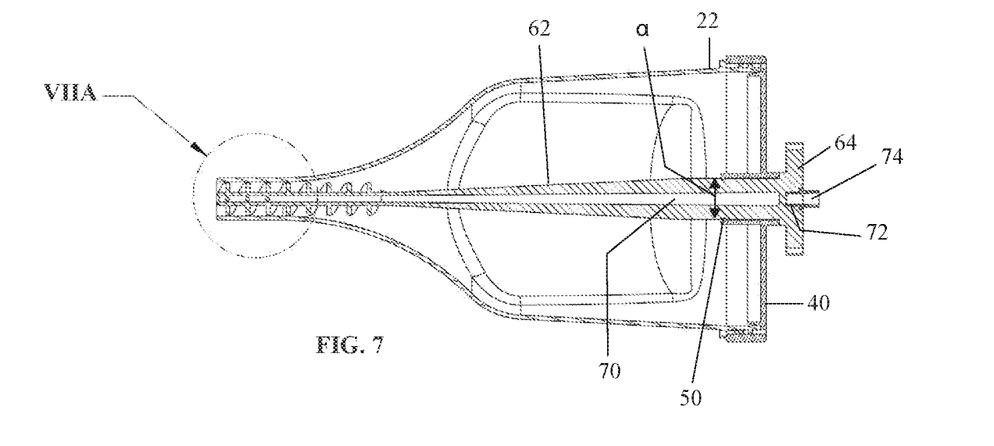
FIG. 7 is a cross-sectional side elevation view of the tool illustrated in FIG. 6, taken along line VII-VII.
Figure 8:
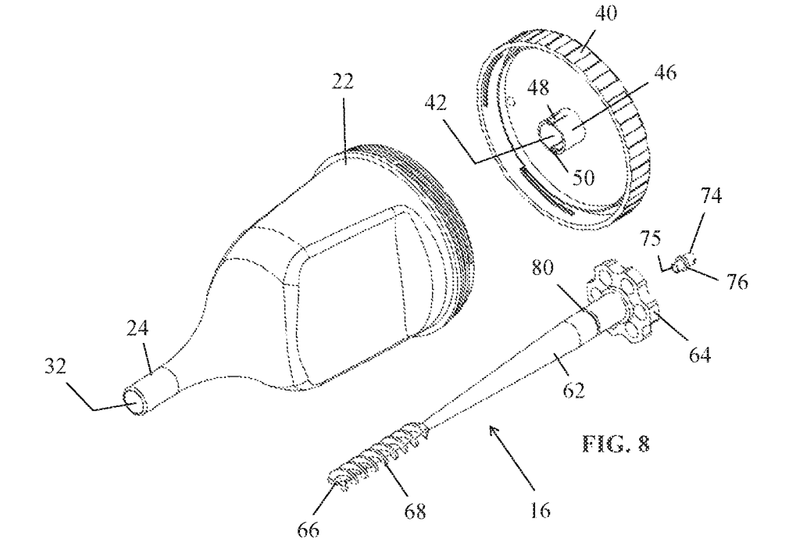
FIG. 8 is an exploded perspective view of the tool illustrated in FIG. 5.
Figure 9:
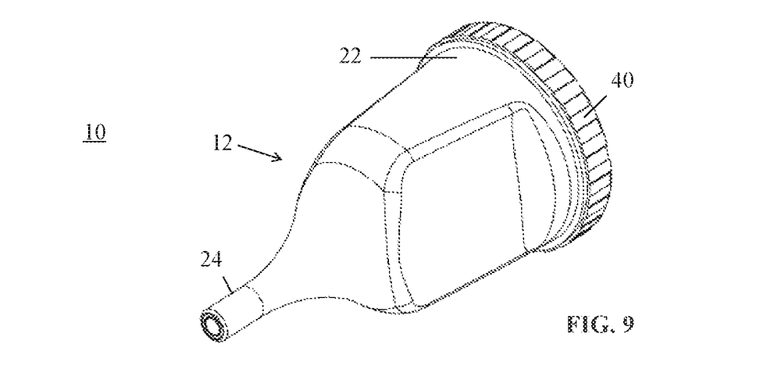
FIG. 9 is a perspective view of the tool of FIG. 1 with the insertion and screw trocars being taken out and a suppository trocar being inserted into the tool, in accordance with the present invention.
Figure 10:
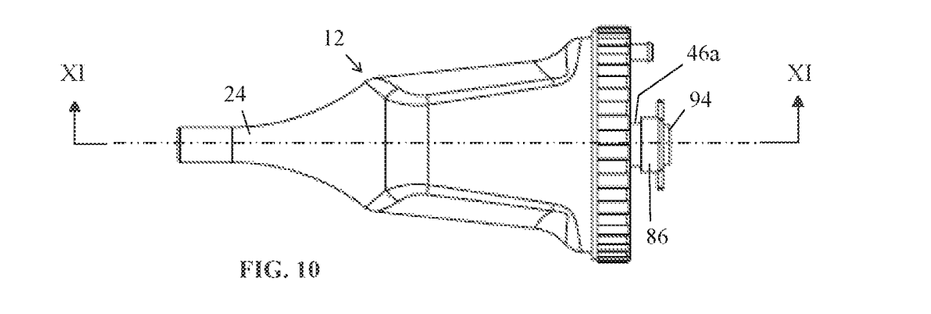
FIG. 10 is a top plan view of the tool illustrated in FIG. 9.

With reference to FIGS. 5-8, the screw trocar 16 when used with the housing 12 will now be described in more detail. The screw trocar 16, as best shown in FIG. 8, comprises a generally circular and elongated rod 62, one end of which including a handle 64 and an opposing end including a tip 66. The rod 62 has a larger diameter in a region of the rod 62 proximal to the handle 64 and has the larger diameter smoothly and substantially diminish towards the tip 66. The larger diameter of the region proximal to the handle 64 is configured to correspond to diameter α of the duct 30 in the rear portion 22 of the housing 12. A region of the rod 62 near the tip 66 and distal to the handle 64 comprises pitched or angled spiral blades 68. In the illustrated embodiment, the spiral blades 68 are right spiral blades having an external diameter corresponding to diameter β (FIG. 3) of the duct 30 in the front portion 24 of the housing 12. Alternatively, the spiral blades 68 can be left spiral blades or helical blades.

Figure 7A:
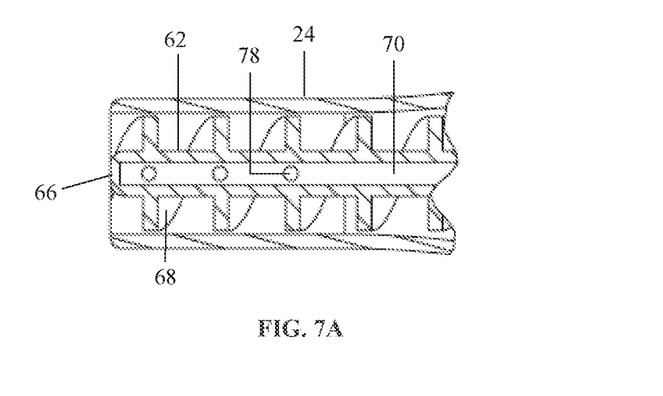
FIG. 7A is an enlarged side view of section VIIA of the tool shown in FIG. 7

As can be best seen in FIGS. 7 and 7A, the rod 62 includes a central blind bore 70 internally extending along a length of the rod 62 and ending at the tip 66. The handle 64 includes a central opening 72 therethrough that is in fluid communication with the bore 70. The handle 64 further includes a tubular lure lock 74 that has a central opening 75 therethrough (FIG. 8). The lure lock 74 is configured to be removably inserted into the central opening 72 of the handle 64 to serve as a connector for a syringe or other device capable of delivering liquid (not shown) and to provide access to the bore 70. The lure lock 74 includes a seal 76 extending around a circumference of the lure lock 74 and serving as a stopper for the lure lock 74 to not fall through the central opening 72 of the handle 64. Although in the illustrated embodiment the handle 64 is a round broach wheel handle, the handle 64 can have various shapes and configurations so long as the handle 64 is configured to enable a user to easily rotate the screw trocar 16 when the screw trocar 16 is fully inserted into the housing 12.

Turning now to FIG. 7A, the region of the rod 62 near the tip 66 includes one or more irrigation holes 78 connected in fluid communication with the bore 70. Whenever the syringe or other device capable of delivering liquid is connected to the lure lock 74 and irrigation liquid, such as water, is delivered into the bore 70, the irrigation liquid exits the bore 70 through the irrigation holes 78 thereby facilitating, assisting or simplifying the axial rotation of the screw trocar 16 in the housing 12.

As shown in FIG. 7, the region of the rod 62 proximal to the handle 64 further includes a notch 80 disposed some distance away and being proximal to the handle 64 of the screw trocar 16. The notch 80 extends around the circumference of the rod 62. When the screw trocar 16 is fully inserted into the housing 12, i.e., through the central opening 42 in the lid 40 and all the way along the duct 30 of the housing 12, the notch 80 aligns with and is configured to engage the detents 50 of the pair of tabs 48. As such, the detents 50 engaged with the notch 60 prevent or limit the screw trocar 16 from having a free or unobstructed linear movement along the duct 30, meanwhile allowing the screw trocar 16 to freely rotate within the duct 30 of the housing 12.

With reference to FIGS. 9-12, the suppository trocar 18 when used with the housing 12 will now be described in more detail. The suppository trocar 18, as best shown in FIG. 12, comprises a sheath 82 and a plunger 84 for removably inserting therein. The sheath 82 is a tubular and elongated beam having a circular cross-section. One end of the sheath 82 includes a handle or ring 86 and the opposite end includes an opening 88 that is connected with a round and hollow channel 90 (FIGS. 11A and 11B) internally extending through the sheath 82. The handle 86 includes a circular opening 87 therethrough that is connected with the hollow channel 90. Further, the handle 86 has one or more internal grooves (not shown) longitudinally extending along the opening 87.

As can be seen in FIG. 12, a substantially longer portion 82a of the sheath 82 has a diameter that is larger than a diameter of the shorter portion 82b of the sheath 82. It should be apparent that the diameter of the longer portion 82a corresponds to diameter α in the rear portion 22 and the region 23 of the housing 12, and the diameter of the shorter portion 82b corresponds to diameter β in the front portion 24 (FIG. 3). As such, the longer and shorter portions 82a, 82b of the sheath 82 are configured to fit inside the duct 30 with minimal or no friction, though some interference fit is possible.

As shown in FIG. 12, the region of the sheath 82 proximal to the handle 86 further includes a notch 92 disposed some distance away and being proximal to the handle 86 of the sheath 82. The notch 92 extends around the circumference of the sheath 82. When the sheath 82 is fully inserted into the housing 12, i.e., through the central opening 42 in the lid 40 and all the way along the duct 30 of the housing 12, as shown in FIGS. 11A and 11B, the notch 92 aligns with and is configured to engage the detents 50 of the pair of tabs 48. As such, the detents 50 engaged with the notch 92 prevent or limit the sheath 82 from having a free or unobstructed linear movement along the duct 30. It should also be noted that the sheath 82 is fully inserted, as shown in FIG. 11B, when the handle 86 abuts the upper portion 46a of the sleeve 46. Thus, the handle 86 also serves as a stopper that limits a further linear movement of the sheath 82 through the sleeve 46.

The plunger 84 comprises a generally circular shaft 94, one end of which including a ring or handle 96 and an opposing end including a tip 98. The shaft 94 has one or more tabs 100 each outwardly extending from the handle 96 and along the shaft 94, as shown in FIG. 12. The shaft 94 has a diameter that is smaller that a diameter of the hollow channel 90 of the sheath 82, such that the shaft 94 of the plunger 84 can be inserted along the hollow channel 90 of the sheath 82, as shown in FIG. 11A. When the one or more tabs 100 of the shaft 94 are aligned with the one or more internal grooves in the handle 86 of the sheath 82, the one or more tabs 100 are configured to slide into the one or more grooves thereby eliminating a length $Y$ (FIG. 11A) of the shaft 86 that is otherwise unable to enter the hollow channel 90. Thus, the one or more tabs 100 serve as stoppers, until aligned with the one or more grooves in the handle 86, for the shaft 94 to be fully inserted into the hollow channel 90 of the sheath 82.

Turning now to FIGS. 11A-12, the opening 88 of the sheath 82 has an internal diameter configured to receive a suppository 102. The suppository 102 can be retained or held within the opening 88 by an interference fit. The suppository 102 can be a glycerin suppository that can melt, soften or liquify a hardened stool in a patient.

In operation, the front portion 24 of the housing 12 can be at least partially inserted into an anal canal or rectum of the patient. The insertion trocar 14 can be used to dent or penetrate the blockage in the patient. The screw trocar 16 can then be used within the housing 12. The screw trocar 16 is rotated within the housing 12 to draw at least some of the blockage of the patient into the internal repository 28 of the housing 12. After that, the screw trocar 16 can be withdrawn and the suppository trocar 18 inserted into the housing 12 to deposit the suppository 102 into the patient to effectuate removal of fecal impaction in the patient.

As can be best seen in FIGS. 11A and 11B, when the front portion 24 of the housing 12 is inserted into the patient, the suppository 102 can be inserted through the opening 87 in the handle 86 of the sheath 82 that is, in turn, fully inserted and extends along the inner duct 30 of the housing 12. The shaft 94 of the plunger 84 can then push the suppository 102 towards the opening 88 of the sheath 82 until the shaft 94 is stopped the length $Y$ away from the upper portion 46a of the sleeve 46 of the lid 40 by the one or more tabs 100. The user of the tool 10 can then align the one or more tabs 100 with the one or more grooves inside the opening 87 in the handle 86 of the sheath 82 and push the plunger 84 further towards the opening 88 of the sheath 82, thereby depositing the suppository 102 into the patient. The step of depositing the suppository 102 into the patient can be performed while slowly pulling the front portion 24 of the housing 12 out of the patient.

Changes and modifications in the specifically described embodiments may be carried out without departing from the principles of the present invention, which is intended to be limited only by the scope of the appended claims, as interpreted according to the principles of patent law including the doctrine of equivalents.

The embodiments of the invention in which an exclusive property or privilege is claimed are defined as follows:

1. A tool for removing fecal impaction in a patient, the tool comprising:
a housing having a front portion, a main body, and a rear portion, the front portion is configured for at least a partial insertion into the patient, wherein the housing includes an internal repository and an inner duct extending from the rear portion to the front portion, and wherein the front portion includes a front opening and the rear portion includes a rear opening;
a screw trocar having a front end and a rear end, the screw trocar can be rotatably and removably inserted into the housing to extend along the inner duct of the housing; and
a suppository trocar having a front end and a rear end, the suppository trocar can be removably inserted into the housing to extend along the inner duct of the housing;
wherein the housing is configured to receive one of the screw or suppository trocars at a time to effectuate removal of fecal impaction in the patient.

2. The tool of claim 1 further comprising an insertion trocar that can be removably inserted into the housing to extend along the inner duct of the housing, wherein the insertion trocar includes a front end and a rear end.

3. The tool of claim 2, wherein the rear end of the insertion trocar includes a handle and the front end of the insertion trocar includes a rounded tip configured to extend a distance past the front portion of the housing when the insertion trocar is fully inserted into the housing.

4. The tool of claim 1, wherein the internal repository is disposed within the main body of the housing, wherein the inner duct extends through the internal repository of the housing, and wherein the rear opening of the housing is in fluid communication with the internal repository.

5. The tool of claim 1 further comprising a lid that is configured to securely cover the rear opening of the housing, the lid including a central opening and a port, wherein the port is configured to be connected to a medical suction device.

6. The tool of claim 1, wherein the front end of the screw trocar includes one or more spiral or helical blades and one or more irrigation openings, and wherein the rear end of the screw trocar includes a handle.

7. The tool of claim 6, wherein the screw trocar includes an internal canal that extends along a length of the screw trocar and is in fluid communication with the one or more irrigation openings, and wherein the internal canal extends through the handle of the screw trocar to form a central opening in the handle.

8. The tool of claim 1, wherein the suppository trocar includes a sheath and a plunger, the sheath having a tubular passage therethrough and the plunger having a shaft that can be removably inserted into the tubular passage of the sheath to extend along a length of the sheath.

9. The tool of claim 8, wherein the sheath includes a front end and a rear end, the front end having a front opening of a first diameter and the rear end having a rear opening of a second diameter, and wherein the rear opening of the sheath is configured to removably receive the shaft of the plunger and the front opening of the sheath is configured to removably receive a suppository.

10. The tool of claim 8, wherein the shaft of the plunger includes a front end and a rear end, and wherein the rear end of the shaft includes a handle and one or more tabs each outwardly extending from the handle and along the shaft.

11. A tool for removing fecal impaction in a patient, the tool comprising:
a housing having a front portion, a main body, and a rear portion, the front portion is configured for at least a partial insertion into the patient, wherein the front portion includes a front opening and the rear portion includes a rear opening, and wherein the housing includes an internal repository and an inner duct extending from the rear opening to the front opening;
an insertion trocar having a front end and a rear end, the insertion trocar can be removably inserted into the housing to extend along the inner duct of the housing;
a screw trocar having a front end and a rear end, the screw trocar can be rotatably and removably inserted into the housing to extend along the inner duct of the housing; and
a suppository trocar having a front end and a rear end, the suppository trocar can be removably inserted into the housing to extend along the inner duct of the housing;
wherein the housing is configured to receive one of the insertion, screw or suppository trocars at a time to effectuate removal of fecal impaction in the patient.

12. The tool of claim 11 further comprising a lid that is configured to securely cover the rear opening of the housing, the lid including a central opening and a port, wherein the port is configured to be connected to a medical suction device.

13. The tool of claim 11, wherein the rear end of the insertion trocar includes a handle and the front end of the insertion trocar includes a rounded tip configured to extend a distance past the front portion of the housing when the insertion trocar is fully inserted into the housing.

14. The tool of claim 11, wherein the front end of the screw trocar includes one or more spiral or helical blades and one or more irrigation openings, and wherein the rear end of the screw trocar includes a handle.

15. The tool of claim 14, wherein the screw trocar includes an internal canal that extends along a length of the screw trocar and is in fluid communication with the one or more irrigation openings, and wherein the internal canal extends through the handle of the screw trocar to form a central opening in the handle.

16. The tool of claim 11, wherein the internal repository is disposed within the main body of the housing, wherein the inner duct extends through the internal repository of the housing, and wherein the internal repository receives fecal matter of the patient when the screw trocar is fully inserted and rotated in the inner duct of the housing.

17. The tool of claim 11, wherein the suppository trocar includes a sheath and a plunger, the sheath having a tubular passage therethrough and the plunger having a shaft that can be removably inserted into the tubular passage of the sheath to extend along a length of the sheath.

18. The tool of claim 17, wherein the sheath includes a front end and a rear end, the front end having a front opening of a first diameter and the rear end having a rear opening of a second diameter, and wherein the rear opening of the sheath is configured to removably receive the shaft of the plunger and the front opening of the sheath is configured to removably receive a suppository.

19. The tool of claim 17, wherein the shaft of the plunger includes a front end and a rear end, and wherein the rear end of the shaft includes a handle and one or more tabs each outwardly extending from the handle and along the shaft.

20. A method of using a tool for removing fecal impaction in a patient, the tool having a housing with a front portion including a front opening, a rear portion including a rear opening, an internal repository, an inner duct extending from the rear opening to the front opening, a screw trocar that can be rotatably and removably inserted into the housing to extend along the inner duct of the housing, and a suppository trocar that can be removably inserted into the housing to extend along the inner duct of the housing, the method comprising:
at least partially inserting the front portion of the housing into the patient;
rotating the screw trocar that extends along the inner duct of the housing to draw at least a portion of a fecal blockage of the patient into the internal repository of the housing;
withdrawing the screw trocar and inserting the suppository trocar to extend along the inner duct of the housing, wherein the suppository trocar holds a suppository to be delivered within the fecal blockage of the patient; and
depositing the suppository within the fecal blockage of the patient to effectuate removal of fecal impaction in the patient.

* * * * *